US010369347B2

(12) United States Patent
Lauer

(10) Patent No.: US 10,369,347 B2
(45) Date of Patent: *Aug. 6, 2019

(54) SCREW CONNECTOR FOR MEDICAL HOSE SYSTEMS AND A MEDICAL HOSE SYSTEM HAVING A SCREW CONNECTOR

(71) Applicant: Fresenius Medical Care Deutschland GmbH, Bad Homburg (DE)

(72) Inventor: Martin Lauer, St. Wendel (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 358 days.

This patent is subject to a terminal disclaimer.

(21) Appl. No.: 15/108,325

(22) PCT Filed: Feb. 24, 2015

(86) PCT No.: PCT/EP2015/053841
§ 371 (c)(1),
(2) Date: Jun. 27, 2016

(87) PCT Pub. No.: WO2015/128325
PCT Pub. Date: Sep. 3, 2015

(65) Prior Publication Data
US 2016/0325086 A1 Nov. 10, 2016

(30) Foreign Application Priority Data
Feb. 27, 2014 (DE) .................. 10 2014 002 650

(51) Int. Cl.
*A61M 39/00* (2006.01)
*A61M 39/10* (2006.01)
(Continued)

(52) U.S. Cl.
CPC ........ *A61M 39/1011* (2013.01); *A61M 39/16* (2013.01); *A61M 1/3661* (2014.02);
(Continued)

(58) Field of Classification Search
CPC ..................... A61M 1/3653; A61M 39/1011; A61M 39/16; A61M 2039/1033; A61M 2039/1044
See application file for complete search history.

(56) References Cited

U.S. PATENT DOCUMENTS 3,952,899 A 4/1976 Cooke
5,096,083 A 3/1992 Shaw
(Continued)

FOREIGN PATENT DOCUMENTS

CN 101918056 12/2010
CN 102164628 8/2011
(Continued)

*Primary Examiner* — Benjamin J Klein
(74) *Attorney, Agent, or Firm* — Jacobson Holman, PLLC.

(57) ABSTRACT

A screw connector includes a first connector with a first lumen and an outside thread, and a second connector with an elastically deformable nut and an inside thread. The outside thread has a first formation and the nut has a second formation, the second formation is a recess in the base of the nut, and the inside thread and the outside thread are configured for mutual connection. The nut is configured for deformation by the first formation in a first angle-of-rotation range without the first formation engaging in the recess, and the inside thread, the outside thread, the first formation, and the recess are configured for engaging the first formation when the inside and outside threads are connected in a second angle-of-rotation range. The screw connector has a half-open sterilization position in the second angle-of-rotation range. In another range, the screw connector may be tightened to be gas-tight and/or liquid-tight.

17 Claims, 7 Drawing Sheets

(51) Int. Cl.
*A61M 39/16* (2006.01)
*F16B 39/30* (2006.01)
*A61M 1/36* (2006.01)

(52) U.S. Cl.
CPC ............... *A61M 2039/1033* (2013.01); *A61M 2039/1044* (2013.01); *F16B 39/30* (2013.01)

(56) References Cited

U.S. PATENT DOCUMENTS

| | | | |
|---|---|---|---|
| 5,650,071 A * | 7/1997 | Brugger | A61M 1/3643 210/646 |
| 6,381,928 B1 | 5/2002 | Gregory | |
| 2011/0028913 A1 * | 2/2011 | Muramatsu | A61M 5/31511 604/222 |
| 2014/0339811 A1 * | 11/2014 | Wong | A61J 1/2096 285/92 |
| 2016/0325087 A1 * | 11/2016 | Lapp | A61M 39/1011 |

FOREIGN PATENT DOCUMENTS

| | | |
|---|---|---|
| DE | 3515665 | 5/1986 |
| DE | 202009013409 | 3/2011 |
| EP | 2314343 | 4/2011 |
| GB | 555123 | 8/1943 |
| JP | 2005000466 | 1/2005 |
| WO | WO 96/40320 | 12/1996 |
| WO | WO 99/20376 | 4/1999 |
| WO | WO 2010/121819 | 10/2010 |

* cited by examiner

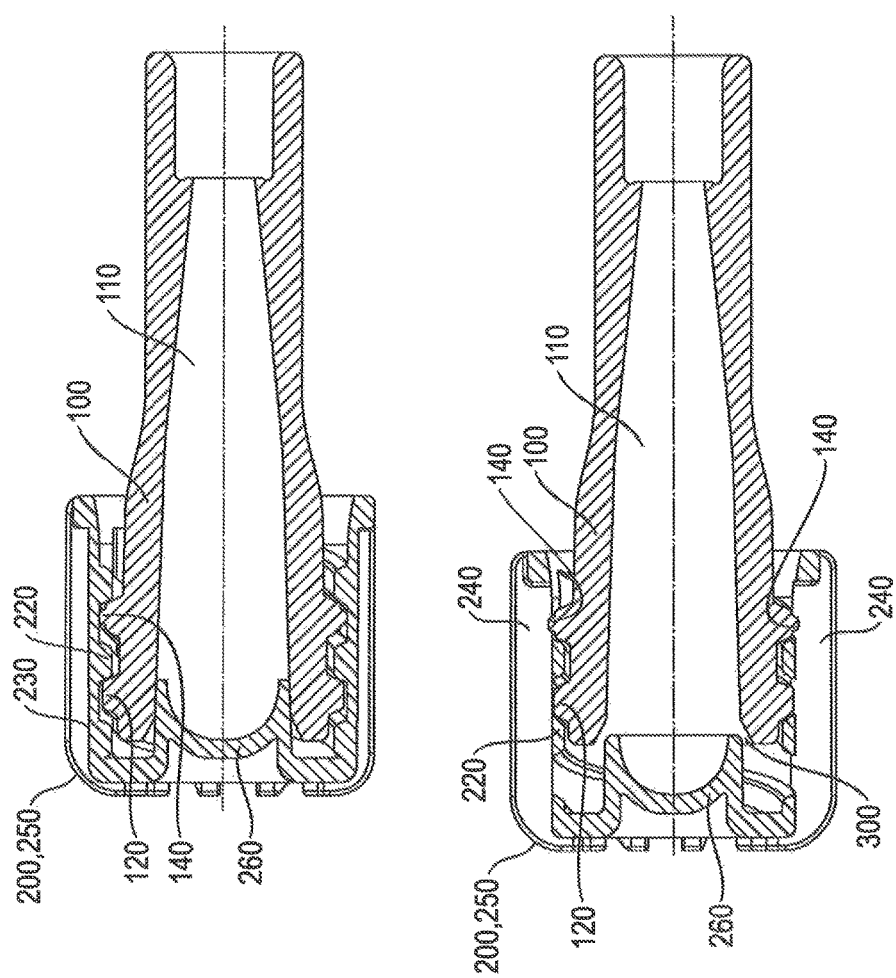

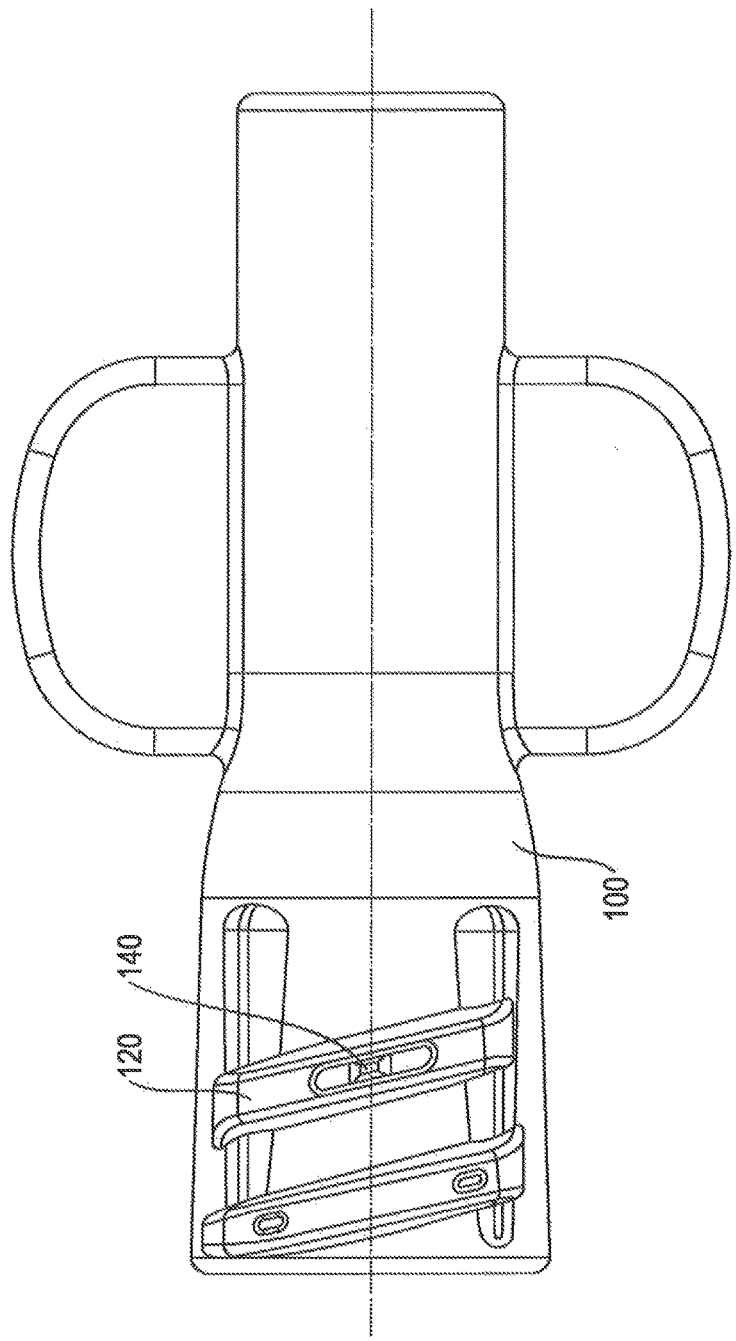

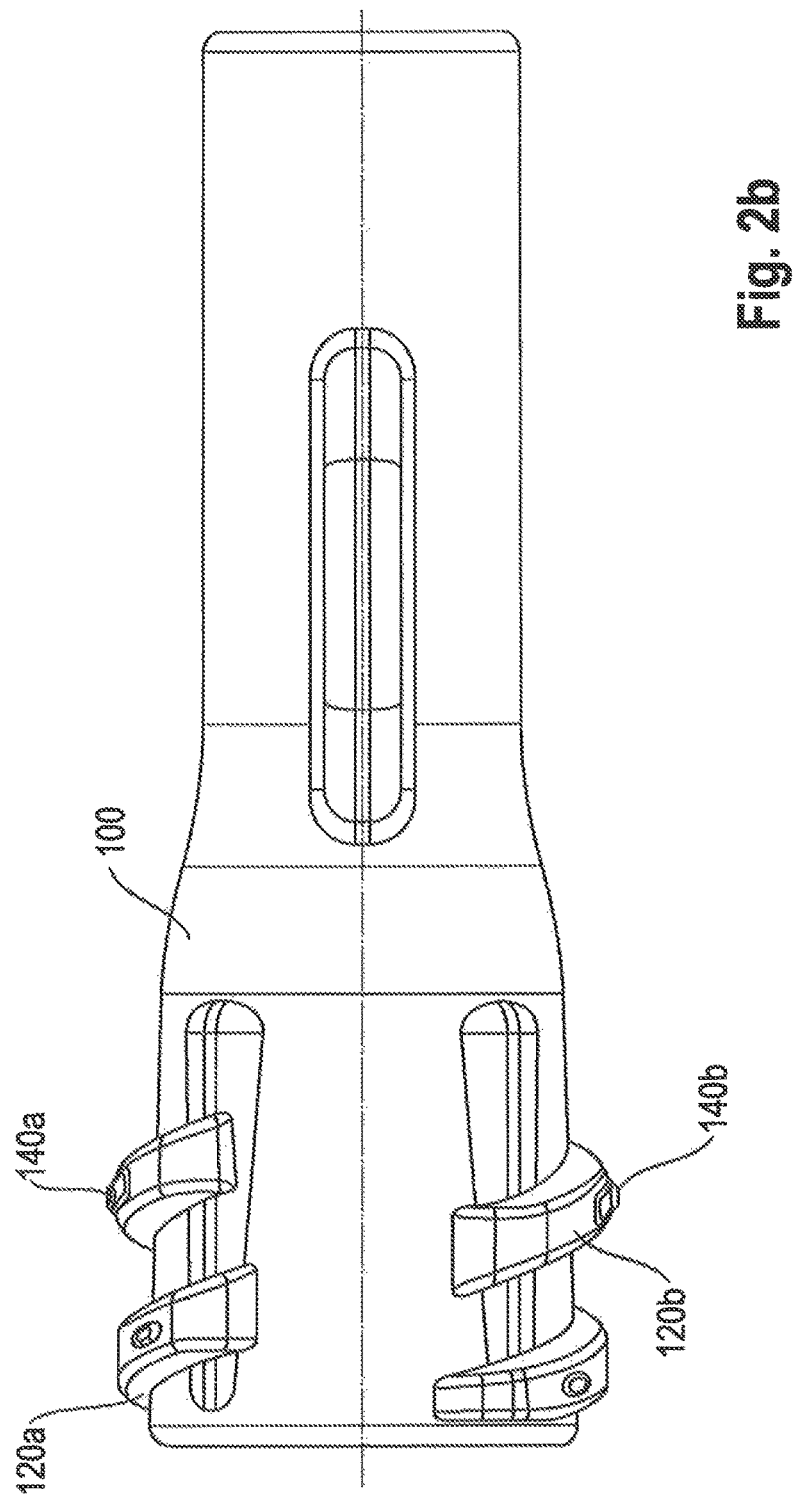

SCREW CONNECTOR FOR MEDICAL HOSE SYSTEMS AND A MEDICAL HOSE SYSTEM HAVING A SCREW CONNECTOR

BACKGROUND OF THE INVENTION

1. Field of the Invention

The invention relates to screw connectors for medical hose systems and medical hose systems having hose connectors as well as sterilization of such medical hose systems by means of steam sterilization and/or gas sterilization. A variety of connectors for medical hose systems are known, in particular those screw connectors that have been standardized as Luer-Lock connectors. Medical hose systems may be used, for example, in infusion technology and in an extracorporeal blood treatment and must be sterile for these applications.

2. Description of Related Art

To ensure the sterility, medical hose systems for infusion technique and extracorporeal blood treatment are packaged in a suitable closed packaging and are sterilized in this packaging. The sterilization may be performed as steam sterilization and/or as gas sterilization, for example. The sterilization methods mentioned above require the gases and/or hot steam to be able to reliably reach all the internal and external surfaces of the medical hose system.

The document DE 35 15 665 C1 discloses a closure stopper for tight sealing of closures in medical technology, in particular Luer-Lock connectors. Both of its connecting parts allow optionally a loose attachment, with which the passage of gas is still possible as well as allowing the connection to be tightly sealed. The loosely attached position and the closed position are separated by a stop which can be overcome by elastic deformation. It is therefore proposed that the stop be designed by means of two internal radial ring ribs in front of the internal thread of the closure stopper and two external wings on the complementary connecting part.

One disadvantage of this known closure stopper is that the two internal radial ring ribs can be overcome only by a compressive force acting on the connecting parts individually and one after the other, axially to the axis of rotation of the closure stopper. If the compressive force does not act precisely axially, then canting may occur. Consequently, the user must align the connecting parts very accurately, which is made difficult by the fact that the ring ribs are arranged directly in front of the inside thread of the closure stopper.

When applying a force that does not act precisely axially or applying an axial force that too small, the closure stopper may fall off and in the worst case may even fall on the floor so that it is no longer sterile. The known closure stopper is therefore unreliable and complicated to handle.

On the whole, this burdens the clinic staff with procedures that are complicated and/or subject to error.

The document WO 99/20376 A1 proposes a method for rinsing a blood hose set for the extracorporeal blood treatment, wherein it is proposed that the patient's arterial connector and the patient's venous connector be connected already during the production of the blood hose set to a connector and that they be sterilized in this connected form.

The document WO 96/40320 A1 proposes another method for rinsing a blood hose set for the extracorporeal blood treatment, wherein it is proposed that the patient's arterial connector and the patient's venous connector be connected to a drain by way of a Y connector in rinsing the blood hose set. To do so it is proposed that the packaged extracorporeal blood hose set should already contain the Y connector connected to the patient's arterial connector and the patient's venous connector.

The document WO 2010/121819 A1 by the applicant of the present patent application discloses a blood cassette having a blood hose set for the extracorporeal blood treatment with a patient's arterial line and a patient's venous line. In addition, the document WO 2010/121819 A1 also discloses a method for rinsing an extracorporeal blood circulation, wherein the patient's connectors of the patient's arterial line and the patient's venous line should be connected to the rinse port of the dialysis machine by means of a T-connector. Reference is made to the contents of the document WO 2010/121819 A1 to the full extent in the present patent application.

Conical connectors having a 6% (Luer) cone for syringes, cannulas and certain other medical instruments, in particular lockable conical connectors, are known and are also referred to as Luer-Lock connectors.

SUMMARY OF THE INVENTION

One object of the present invention is therefore to overcome at least one of the aforementioned disadvantages and to provide an improved screw connector for medical hose systems.

This object is achieved with the features of the invention as described herein. Advantageous embodiments of the invention are also as described herein.

The present invention relates to a screw connector for a medical hose system having a first connecting element with a first lumen and an outside thread and a second connecting element with an elastically deformable nut with an inside thread, wherein the inside thread and the outside thread are configured to be screwed together, wherein the outside thread has a first formation and the nut has a second formation, wherein the second formation is a recess in the base of the thread of the nut. The inside thread and the outside thread are configured for mutual screwing and the nut is configured for elastic deformation through the first formation in a predetermined first rotational angle range without the first formation engaging in the recess in the base of the thread of the nut. The outside thread and the first formation and the recess in the base of the thread of the nut are configured for engaging the first formation in the recess in the base of the thread of the nut when the inside thread and the outside thread are screwed together in a predetermined second rotational angle range.

The term "screw connector" in conjunction with the present invention is not limited to a certain embodiment of the liquid-tight connection of a first lumen with a second lumen. The liquid-tight connection, in particular by sealing faces, may be independent of the screw connection and/or may be present in addition to the screw connection. The screw connection may comprise in particular an additional securing means and/or locking means for securing a liquid-tight connection of a first lumen to a second lumen to prevent intentional release.

In one embodiment the first connecting element and the second connecting element are each designed as complementary halves of a common Luer-Lock connector. The inside thread and the outside thread are each embodied as complementary threads on the Luer-Lock connector and serve as an additional means of securing the Luer cone to prevent unintentional release. The complementary threads of a Luer-Lock connector are embodied to be compatible at least with regard to the shape of the thread, the thread diameter, the thread pitch and the thread length and thus are configured and provided for mutual screwing.

The threaded nut of the screw connector is preferably compatible with the complementary halves of standardized connectors because the second formation at the base of the thread of the inside thread of the threaded nut does not cause interference with respect to the complementary halves of standardized connectors, so that, for example, a screw connection of standardized Luer connectors as well as dialysis needles, cannulas, catheters or ports with the threaded nut according to the invention is not impaired.

The outside thread preferably has a first formation, which is a local elevation on the thread flank of the outside thread, predominantly or exclusively on the outside diameter of the outside thread in particular. This yields an enlarged diameter of the outside thread locally in the area of the elevation.

In one embodiment, the first formation on the thread flank of the outside thread is a nose or a lobe. The diameter of the outside thread is then enlarged only in the area of the lobe or the nose.

In another embodiment, the first formation comprises multiple local elevations on the thread flank of the outside thread spaced a distance apart from one another. The diameter of the outside thread is then increased in the area of each of the local elevations.

In another embodiment, the first formation comprises multiple noses or lobes on the thread flank of the outside thread. The diameter of the outside thread is then enlarged in the area of each of the lobes or noses.

The nut has a second formation, which is a recess in the base of the thread of the nut.

In one embodiment, the second formation is a depression in the base of the thread of the nut. The diameter of the base of the thread of the inside thread in the area of the depression is therefore greater than that in other sections of the nut.

In another embodiment, the second formation comprises at least one through-opening in the base of the thread of the nut between the interior of the nut and an external environment of the nut. Such an embodiment is especially advantageously to be produced by injection molding because the core mold for the through-opening can be unmolded with no problem.

In another embodiment, the second formation comprises at least one radial groove in an axial end face of the nut, wherein the radial groove is open in the direction of the axial end face of the nut. Such an embodiment is especially advantageous for production by injection molding because the core mold for the radial groove can be unmolded with no problem.

In accordance with the teaching of the present invention, the nut is configured for elastic deformation through the first formation in a predefined first angle-of-rotation range, in which the first formation does not engage in the recess in the base of the thread of the nut. The diameter of the nut can therefore be widened elastically in twisting in a first angle-of-rotation range if a lobe or nose on the thread flank of the outside thread presses against the base of the thread of the nut in the interior of the nut and/or slides along the base of the thread. In other words, the first formation in the predetermined first angle-of-rotation range does not strike a second formation, so that the first formation in the predetermined first angle-of-rotation range cannot engage in a second formation. The inside thread and the outside thread and the first formation and the recess in the base of the thread of the nut are additionally configured for engaging the first formation in the recess in the base of the thread of the nut when the inside thread and the outside thread are screwed together in a predefined second angle-of-rotation range. For example, a lobe or a nose on the thread flank of the outside thread will engage in the recess in the base of the thread of the nut when the inside thread and the outside thread are screwed together in a predefined second angle-of-rotation range. On engagement in the second angle-of-rotation range, the elastic deformation of the nut is reversible because there is not a lobe or a nose on the thread flank of the outside thread pressing against the base of the thread of the nut in the interior of the nut. The second angle-of-rotation range may be defined by the shape and the arrangement of the first and/or second formations.

In one embodiment, the nut has at least one reinforcing rib arranged in the axial direction of the nut on its outer circumference, such that the at least one through-opening extends at least partially along the reinforcing rib.

In another embodiment, a plurality of reinforcing ribs is arranged on the outer circumference of the nut in the axial direction of the nut such that the at least one through-opening extends at least partially along and between two reinforcing ribs.

In another embodiment, the second connecting element has a sealing cap with a sealing structure or it is a sealing cap with a sealing structure. Such an embodiment may exist, for example, when the second connecting element is configured as a touch protection cap and/or a closing cap. The sealing structure may be configured for gas-tight and/or liquid-tight sealing with a first connecting element.

In another embodiment, the first lumen is designed as the female half of a Luer connector or a Luer-Lock connector and the sealing structure is designed as the male half of the Luer connector.

In another embodiment, the second connecting element has a lumen which is referred to as the second lumen and the nut is configured as a union nut. The union nut is supported on a second connecting element so that it can be rotated so that the union nut can be screwed onto a first connecting element without causing the second connecting element to rotate. Such an embodiment is especially advantageous when the screw connector according to the invention is provided for connecting two hose line sections which should not twist in screw connection of the screw connector.

In another embodiment, the first lumen is designed as the female half of a Luer connector and the second lumen is designed as the male half of the Luer connector.

One advantage of the present invention is that a screw connector is provided for medical hose systems, which allows a half-open sterilization position and at the same time is ergonomic and reliable in handling. The half-open sterilization position is reliable and secure at the same time.

In many embodiments, a half-open sterilization position may be understood to mean that the two complementary halves of a Luer-Lock connector are not connected so as to form a seal, but instead there is a defined gap between the complementary conical surfaces of the Luer-Lock connector. Therefore, in steam and/or gas sterilization, the steam and/or the gas can enter through the gap between the complementary halves into the respective interior of the complementary halves of the Luer-Lock connector. The term "half-open" is used to make it clear that the two complementary halves of the Luer-Lock connector are each at least partially covered by the complementary half of the Luer-Lock connector. This has the advantage that touch protection is ensured for both complementary halves of the Luer connector despite the defined gap without requiring additional touch protection caps to do so.

In many embodiments, the half-open sterilization position may have the advantage that the two complementary halves of the Luer-Lock connector are already preassembled and need only be connected with a seal for the application and secured by screw connections. Such embodiments are especially user friendly because the work of connecting the Luer connector is facilitated for the user and/or the user is at least partially relieved of doing such work.

In another embodiment, the screw connector is configured to be screwed to form a gas-tight and/or liquid-tight connection in a wider angle-of-rotation range, for example, a third angle-of-rotation range, wherein the first connecting element and the second connecting element are each configured to be gas-permeable when screwing the inside thread to the outside thread in the second angle-of-rotation range between an external environment of the screw connector and an interior of the screw connector formed at least by the first lumen. Furthermore, the first connecting element and the second connecting element are each configured to form a gas-tight and/or liquid-tight seal between the outside environment of the screw connector and the interior of the screw connector when forming the screw connection of the inside thread with the outside thread in the wider angle-of-rotation range. For screw connection in the wider angle-of-rotation range, first it is necessary to exceed the second angle-of-rotation range. In other words, the screw connector is turned further beyond the second angle-of-rotation range. In doing so, the first formation is first disconnected from the second formation. For the disengagement of the first formation from the second formation, a torque must be applied to the nut. The gas-tight and/or liquid-tight position is reached only by completely tightening the screw connection.

In many embodiments, the second angle range may be determined essentially by the width of the first formation and the width of the second formation in the angle of rotation of the thread. The second formation may have an excess in comparison with the first formation, thus resulting in play. This play may facilitate the catch engagement of the first formation in the second formation.

In another embodiment, the screw connector according to the invention is part of a medical hose system. The term "medical hose system" in the present invention comprises all medical products having at least one hose section and being configured and/or provided in particular for the extracorporeal blood treatment, in particular for hemodialysis, hemofiltration or hemodiafiltration or for peritoneal dialysis or for infusion of medical solutions into the patient.

One embodiment of the medical hose system according to the invention is a blood hose set for the extracorporeal blood treatment with a patient's arterial hose and a patient's venous hose, wherein at least the patient's end of the patient's venous hose and/or the patient's end of the patient's arterial hose is/are embodied as the first connecting element or the second connecting element of the screw connector according to the invention.

Another advantage of the present invention is that a preconnected blood hose set for the extracorporeal blood treatment is provided with a three-way connector, which permits a half-open sterilization position of the Luer-Lock connections of the arterial and patient's venous connector preconnected to the three-way connector while at the same time being ergonomic and reliable in handling. This yields the additional advantage that two closing caps can be eliminated for closing the arterial and patient's venous connector.

The inventor of the present invention has recognized that the complementary halves of a screw connector of a medical hose set which is different from the standard should not only be usable to a restricted extent for use in the clinic but instead should be as flexible as possible and in particular should be compatible or even cross-compatible.

In a certain embodiment of the screw connector, both the first connecting element and the second connecting element are each compatible with a mating piece of a standardized Luer-Lock connector for fluid-tight screw connection because neither the first formation nor the second formation has an interfering effect here. One half of the screw connector according to the invention may thus be connected in the clinic to a mating piece of a standardized Luer-Lock connector. The use of the screw connector according to the invention in sterilizing a medical hose set therefore does not limit the use of the medical hose set in the clinic. Therefore the first connecting element and the second connecting element are both cross-compatible and are therefore flexible in use in clinic operation. As one example, dialysis needles, which have a short hose section with one-half of a standardized Luer-Lock connector, can be mentioned. These connectors can be connected to the complementary mating piece of a screw connector according to the invention without any restriction and can be provided for such a connection. The halves of the screw connector according to the invention on the patient's venous line and/or the patient's arterial line can therefore be connected to without restriction to the complementary half of a standardized Luer-Lock connector of an arterial dialysis needle and/or a venous dialysis needle.

The halves of the screw connector according to the invention are each therefore cross-compatible with the complementary halves of a certain standardized screw connector.

The screw connector is preferably insensitive to axial pressure or tension on a first and/or second connecting element when the inside thread has been screwed to the outside thread. The screw connector is then sturdy with respect to unintentional disconnection because of tensile and/or bending stresses on the connecting parts such as those which may occur during packaging, storage and shipping because the threaded flanks absorb the tensile and bending forces. Release is then possible only through a targeted rotational movement beyond the resistance.

The elastic deformation of the nut or union nut in screw connection in the first angle-of-rotation range amounts to less than five-tenths of a millimeter, for example, or more than five-hundredths of a millimeter. The outside diameter of the outside thread of the first connecting element preferably has an excess dimension of 0.1 mm to 0.3 mm in the area of the first formation with respect to the diameter of the base of the thread of the inside thread of the second connecting element, which is embodied, for example, as a nut or a union nut. In other words, a radial excess dimension of preferably 0.05 mm to 0.15 mm is obtained between a first formation and the diameter of the base of the thread of the inside thread of the second connecting element. This excess dimension leads to elastic deformation of the nut or the union nut due to the first formation in the case of mutual screw connection of the inside thread to the outside thread in the predefined first angle-of-rotation range, in which the first formation does not engage in the second formation in the base of the thread of the nut.

The screw connector may be configured for only one single engagement of the first formation in the second formation in one embodiment. In such embodiments, there is no provision for repeated engagement because the first formation and/or the second formation become worn out in engagement and screw connection beyond the engagement. Such embodiments are particularly inexpensive because of the low demands regarding stability of the first formation and/or the second formation.

In one embodiment of the screw connector, a guide aid and/or guide distance is provided, facilitating handling by the user in the clinic and also permitting assembly by robots. In many embodiments the guide aid may be implemented by the thread itself.

One advantage of the present invention is that it makes available a screw connector that is ergonomic and reliable in handling.

The halves of the screw connector may be guided and held reliably in manual screw connection and disconnection in the clinic, which is especially advantageous when the screw connector involves small parts. The outside diameter of the nut of the screw connector according to the invention may be 6 millimeters to 15 millimeters, for example.

For larger screw connectors, the outside diameter may be 15 millimeters to 25 millimeters.

The manual tightening and unscrewing of the screw connector according to the invention typically takes place by twisting the nut or the union nut of the second connecting element between the tips of the thumb and index finger of one hand of the user while the first connecting element is held by the fingers of the other hand. In tightening and/or unscrewing the screw connector according to the invention, the user can sense from the beginning that the first connecting element is rotated by an angle of rotation with respect to the second connecting element and is guided securely by the thread. Secondly, the user feels a change in resistance in turning the connector depending on the angle of rotation, for example, for the first time when the nut or union nut is rotated in the predefined first angle-of-rotation range with its elastic deformation due to the first formation without the first formation engaging in the recess in the base of the thread of the nut and for the second time when the first formation engages in the recess in the base of the thread of the nut when the inside thread and the outside thread are screwed in a predefined second angle-of-rotation range. In addition, the user senses an altered resistance in turning the connector when the inside thread and the outside thread are screwed beyond the predefined second angle-of-rotation range and are tightened in a fluid-tight connection. The user can sense these changes in resistance also when unscrewing the connector until the first connecting element is separated from the second connecting element. When the screw connector has multiple locking positions, the user can sense the altered resistance in each locking position.

The screw connector thus permits a tactile feedback in the manual handling of the screw connector according to the invention due to the rotational resistance, which depends on the angle of rotation, i.e., imparting the sensation of being able to perceive the progress in handling by using one's fingers. It is advantageous here that the distance between the locked state and the unlocked state and vice versa is lengthened by the thread.

The screw connector according to the invention is thus advantageously also ergonomic and reliable to handle.

The nut or the union nut of the second connecting element may be configured by the selection of a suitable elastic material and the shaping for elastic deformation by the first formation of the first connecting element.

Plastics, for example, are suitable as the material for the first connecting element and the second connecting element.

The suitable material for the first and second connecting elements in many embodiments is in particular PP (polypropylene), PC (polycarbonate), PVC (polyvinyl chloride) or ABS (acrylonitrile-butadiene-styrene).

BRIEF DESCRIPTION OF THE DRAWINGS

One exemplary embodiment according to the present teaching is described in greater detail below with reference to the drawings. Additional details and advantages are described further on the basis of the exemplary embodiment illustrated in the figures. The reference numerals used in the drawings have the same meanings in all the drawings.

They show:

FIG. 1 shows a sectional diagram of a first exemplary embodiment of the screw connector according to the invention.

FIG. 2a shows a first view of the first connecting element according to the first exemplary embodiment from FIG. 1.

FIG. 2b shows a 90° rotated second view of the first connecting element according to the first exemplary embodiment from FIG. 1.

DETAILED DESCRIPTION OF THE PREFERRED EMBODIMENTS

Figure 3:
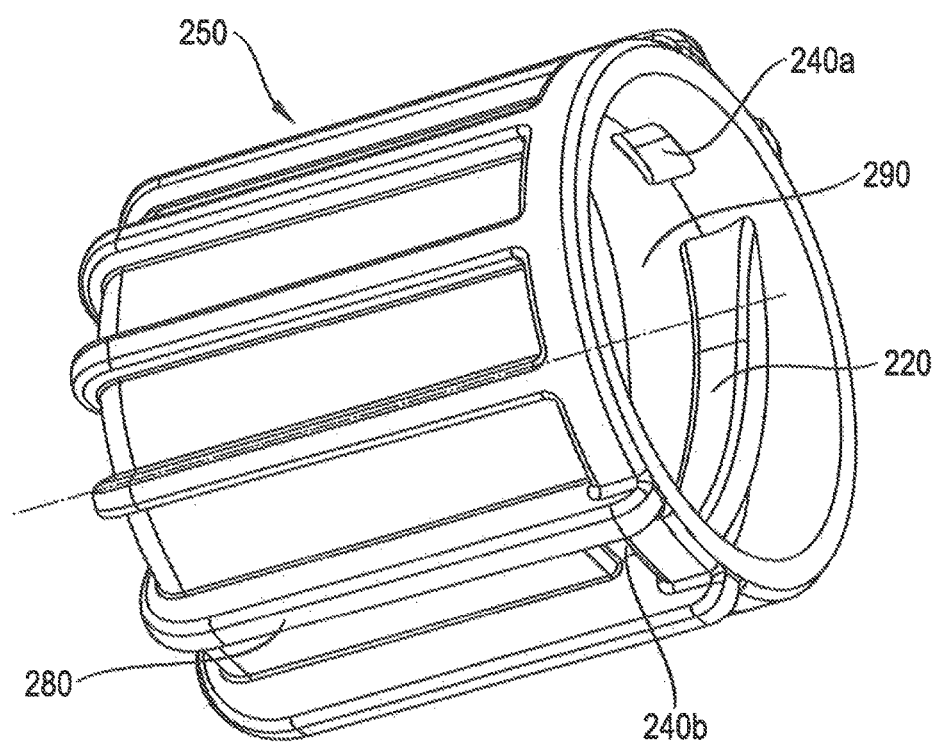
FIG. 3 shows a view of a first exemplary embodiment of the second connecting element according to the first exemplary embodiment of the screw connector according to the invention from FIG. 1.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows a sectional diagram of a first exemplary embodiment of a screw connector in a closed, screwed-in position (top half of the figure) and in a half-open sterilization position (bottom half of the figure). The screw connector has a first connecting element 100, designed as a female half of a Luer connector, with a first lumen 110 and an outside thread 120 as well as a second connecting element 200 in the form of a sealing cap 250 designed as the male half of a Luer connector with an inside thread 220 and a sealing structure 260. The second connecting element is designed as a closing cap or a sealing cap in the form of a nut 230. The outside thread 120 has at least one first formation 140. The first formation is arranged as a local elevation, for example, as a lobe or a nose on the thread flank of the outside thread 120 and protrudes beyond the thread diameter of the outside thread. The inside thread 220 has a second formation 240 where the second formation has a recess in the base of the thread of the nut 230. The recess in the base of the thread of the nut in this exemplary embodiment is designed as a through-opening between the interior of the nut and an external environment of the nut.

The inside thread 220 and the outside thread 120 are configured for mutual screw connection and the nut 230 is configured for elastic deformation by the first formation in a predetermined first angle-of-rotation range without the first formation engaging in the recess in the base of the thread of the nut. The inside thread 220 and the outside thread 120 as well as the first formation and the recess in the base of the thread of the nut are configured for engagement of the first formation in the recess in the base of the thread of the nut when the inside thread and the outside thread are screwed together in a predetermined second angle-of-rotation range (bottom drawing in FIG. 1). The nut 230 is made of an elastically deformable plastic, for example, PP (polypropylene) which permits elastic deformation of the nut 230 by the first formation in the predetermined first angle-of-rotation range. The drawing at the top in FIG. 1 shows the screw connector screwed to a gas-tight and/or liquid-tight condition. The sealing structure 260 is in sealing contact with the inside surface of the first lumen 110 over its entire circumference and seals the first lumen 110 with respect to an external environment of the screw connector. The bottom illustration in FIG. 1 shows the screw connector in the half-open sterilization position in which a gap 300 remains between the first lumen 110 and the sealing structure 260, permitting the passage of gas and steam. Thus the sterilization gas and/or the sterilization steam can penetrate into the lumen 110 during sterilization and can sterilize the surfaces.

The first connecting element and the second connecting element may preferably be configured so that the gap between the conical sealing surfaces of the complementary halves of the Luer-Lock connector in the half-open sterilization position defines a flow cross-sectional area for the admission of the steam and/or gas through the gap into the respective interior of the complementary halves of the Luer connector which corresponds by amount at least to the narrowest flow cross-sectional area of the first connecting element or of the second connecting element. In the case of a Luer-Lock connector the flow cross-sectional area for the admission of the steam and/or gas through the gap into the respective interior of the complementary halves of the Luer connector may, for example, be at least as large as the flow cross-sectional area of the lumen of the male half of the Luer connector.

FIGS. 2a and 2b show a first view of an alternative embodiment of a first connecting element 100 and a second view of the first connecting element 100 which is rotated by 90° about the longitudinal axis of the first connecting element with respect to the first view. The outside thread 120 has at least two first formations 140a, 140b. The first formations 140 are arranged as local elevations, for example, as lobes or noses on the threaded flank of the outside thread 120, and protrude beyond the thread diameter of the outside thread.

In other embodiments, the screw connector may have only a single first formation.

FIG. 3 shows a perspective view of the second connecting element 200 which is embodied as a sealing cap 250. The sealing cap 250 is reinforced by means of reinforcing ribs 280 running in the axial direction of the sealing cap on its outside circumference and over its entire length, these ribs also improving the grip in manual screw connection. FIG. 3 shows a part of the inside thread 220 and opposing second formations 240a and 240b are also visible, embodied as local through-openings in the base 290 of the thread.

Figure 4:
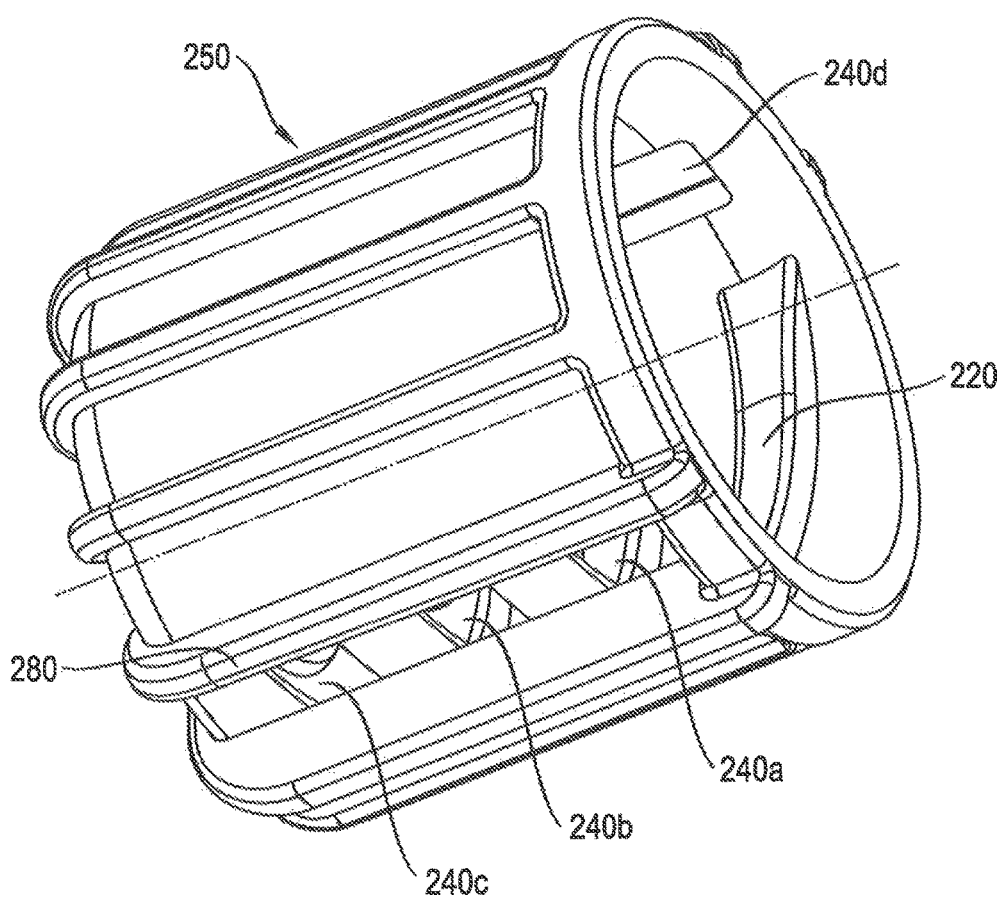
FIG. 4 shows a view of a second exemplary embodiment of the second connecting element according to the first exemplary embodiment of the screw connector according to the invention from FIG. 1.

FIG. 4 shows an alternative embodiment of the second connecting element from FIG. 3, where multiple second formations are provided in the axial direction of the sealing cap 250, extending as multiple through-openings 240a, 240b, 240c and 240d in the base of the thread between neighboring reinforcing ribs 280, as the only difference in comparison with the exemplary embodiment from FIG. 3. This embodiment permits multiple separate catch positions depending on the screw depth of the thread.

Figure 5:
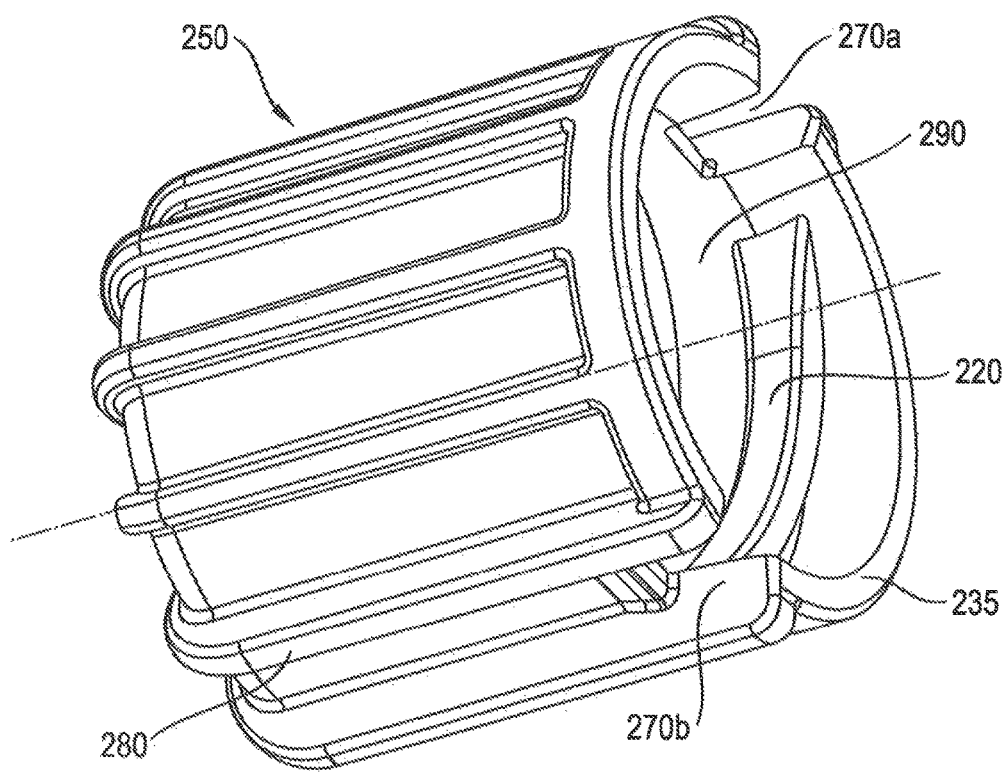
FIG. 5 shows a view of a third exemplary embodiment of the second connecting element according to the first exemplary embodiment of the screw connector according to the invention from FIG. 1.

FIG. 5 shows another alternative embodiment of the second connecting element from FIG. 3, wherein as the only difference from the embodiment in FIG. 3 the second formations are embodied as radial grooves 270a and 270b in the open axial end face of the sealing cap 250 and wherein the radial grooves 270a and 270b are open in the direction of the open axial end face of the nut 230. This embodiment is especially advantageous with regard to the formation in injection molding.

Figure 6:
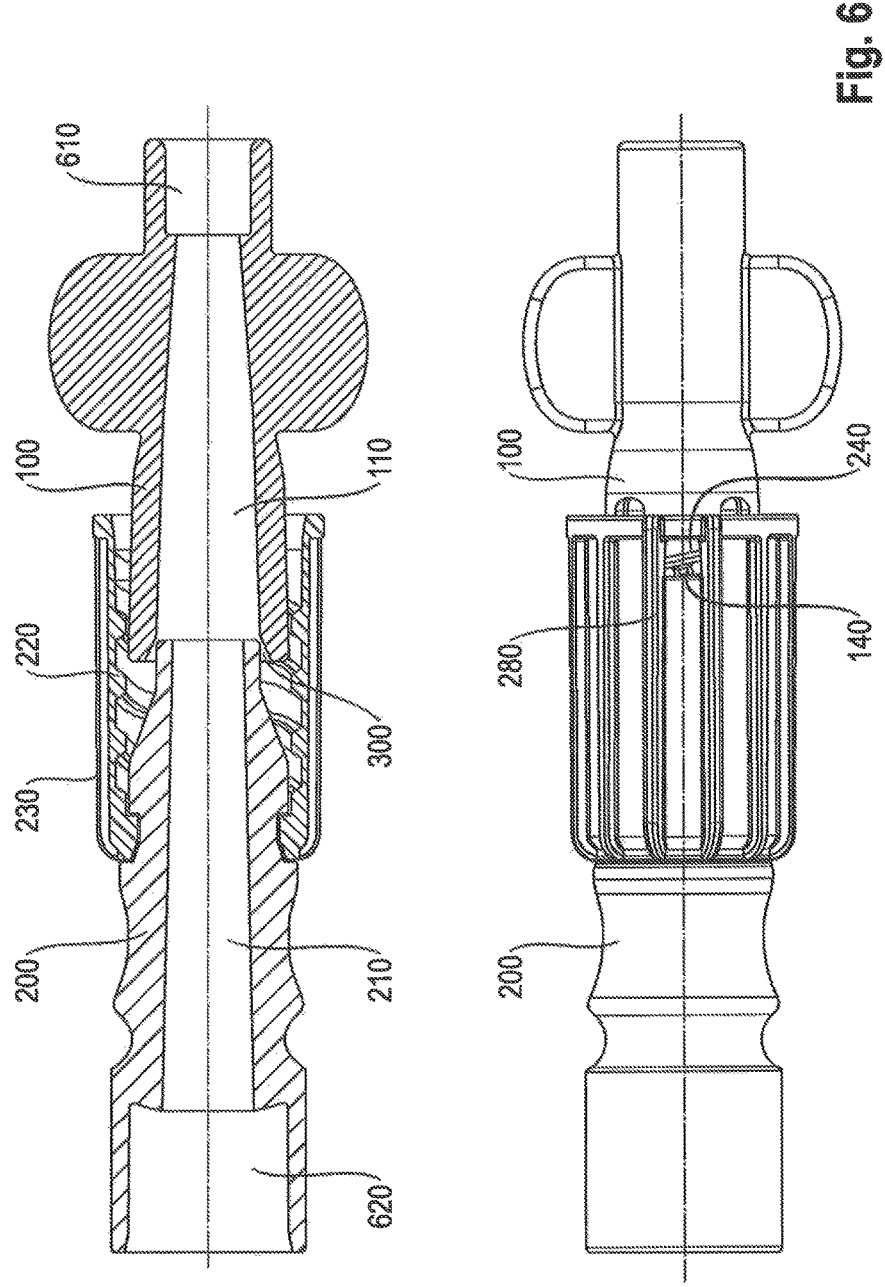
FIG. 6 shows a sectional diagram and a view of a second exemplary embodiment of the screw connector according to the invention.

FIG. 6 shows in the top illustration a section and in the bottom illustration a view of an alternative embodiment of the second connecting element 200 in combination with the embodiment of the first connecting element 100 from FIGS. 2a and 2b, wherein the second connecting element 200 has a second lumen 210 and a nut 230 which is embodied as a union nut. The union nut is rotatably mounted on the second connecting element 200, so that a screw connection of the union nut with the first connecting element 100 is possible without the entire second connecting element 200 having to also turn together with the union nut. The second connecting element 100 has on its free end a first hose receptacle 610 and the second connecting element 200 has on its free end a second hose receptacle 620, each being provided for gluing in hose sections (not shown). The first lumen is designed as the female half of a Luer connector and the second lumen is designed as the male half of the Luer connector.

The screw connectors from FIGS. 1 through 6 may be used on medical hose systems and are provided for that purpose.

For example, the screw connectors according to FIGS. 1 to 6 may be used on hose sets for the extracorporeal blood treatment. Blood hose systems for the extracorporeal blood treatment have at least one patient hose when using a single-needle access or a patient's arterial hose and a patient's venous hose when using a two-needle access. The respective patient's end of each patient hose may be equipped with a screw connector according to the invention or half of a screw connector according to the invention.

Many extracorporeal blood hose sets have at least one feed line for adding a medication into the extracorporeal blood circulation, for example, a heparin line and/or a citrate line and/or a calcium line. The free end of the feed line may be equipped with a screw connector according to FIGS. 1 to 6.

It is also possible to equip a sampling site on a medical hose system with a screw connector according to FIGS. 1 to 6.

In certain embodiments of an extracorporeal blood circulation, the end of the patients arterial hose opposite the patient's end of the patient's arterial hose and the end of the patient's venous hose opposite the patient's end of the patient's venous hose are both connected to a blood cassette for the extracorporeal blood treatment. In many of these embodiments of an extracorporeal blood hose set with a blood cassette, the patient's ends of the patient's arterial hose and of the patient's venous hose are already connected to two free connections of a T-connector at the time of production of the extracorporeal blood hose set, wherein the T-connector is provided for filling and rinsing the blood hose set with priming fluid before the start of the extracorporeal blood treatment. In such embodiments, at least two free connections of the T-connector and the patient's ends of the two patient hoses may be equipped with the complementary halves of a screw connector according to FIGS. 1 to 6. The patient's ends of the patient's arterial hose and of the patient's venous hose are then connected to two free connections of a T-connector already at the time of production of the extracorporeal blood hose set in a half-open sterilization position so that in sterilization of the extracorporeal blood hose set, sterilization gas and/or sterilization steam can penetrate through the gap of the screw connector. The third connection of the T-connector may be sealed by means of a conventional sealing cap or may be equipped with a screw connector according to the present invention. Before sterilization, the extracorporeal blood hose set is packaged in a sterile package. Before use of the extracorporeal blood hose set, the sterile package is opened and the extracorporeal blood hose set is removed. In this state, the screw connectors according to the invention are still in the half-open sterilization position. The two screw connectors on the T-connector may be tightened manually by the user in the clinic, and the free third connection of the rinsing plug connector is connected to a source for priming fluid. After priming and rinsing the extracorporeal blood circulation, the patient's ends of the two patient hoses are unscrewed from the T-connector and are available for connection to the access needles, for example, with an arterial dialysis needle and a venous dialysis needle.

Special embodiments (not shown) of the second connecting element, for example, the male half of the Luer-Lock connector with a nut rigidly connected in one piece such as those known without the second formation of Luer-Lock syringes, for example, are also consistent with the teaching of the present invention. Such special embodiments of the second connecting element can be manufactured by injection molding with a second formation. Such embodiments may be part of a container, a drip chamber or a medical fluid cassette, for example, in particular a dialysis cassette for the extracorporeal blood treatment, and they permit a direct connection of a hose section to a first connecting element with a first formation in the half-open sterilization position.

In automated production of medical hose systems, in particular in automated production of blood hose sets for the extracorporeal blood treatment, the use of a screw connector according to the teaching of the present invention is especially advantageous due to the easy-to-assemble construction of the individual parts for assembly by robots.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

LIST OF REFERENCE NUMERALS

| Numeral | Name |
| --- | --- |
| 100 | first connecting element |
| 110 | first lumen |
| 120, 120a, 120b | outside thread |
| 130 | base of thread |
| 140, 140a, 140b | first formation |
| 200 | second connecting element |
| 210 | second lumen |
| 220 | inside thread |
| 230 | nut |
| 235 | end face |
| 240, 240a, 240b, 240c, 240d | second formation |
| 250 | sealing cap |
| 260 | sealing structure |
| 270, 270a, 270b | radial groove |
| 280 | reinforcing rib |
| 290 | base of thread |
| 300 | gap |
| 400 | three-way connector |
| 500 | medical hose set |
| 510 | patient's arterial line |
| 511 | patient's end of the patient's arterial line |
| 520 | patient's venous line |
| 521 | patient's end of the patient's venous line |
| 610 | first hose receptacle |
| 620 | second hose receptacle |

What is claimed is:

1. A screw connector for a medical hose system, comprising
a first connecting element with a first lumen and an outside thread and
a second connecting element with an elastically deformable nut with an inside thread,
the inside thread and the outside thread being configured to be screwed to one another,
with the outside thread having a first formation and the nut having a second formation, with the second formation being a recess in a base of the thread of the nut, and
the inside thread and the outside thread being configured for mutual screw connection, and the nut being configured for elastic deformation by the first formation in a predetermined first angle-of-rotation range without the first formation engaging in the recess in the base of the thread of the nut, and
the inside thread and the outside thread and the first formation and the recess in the base of the thread of the nut being configured for engaging the first formation in the recess in the base of the thread of the nut when the inside thread and the outside thread are screwed together in a predetermined second angle-of-rotation range,
with the first connecting element and the second connecting element each being configured to be gas-permeable when the inside thread is screwed to the outside thread in the second angle-of-rotation range between an external environment of the screw connector and an interior of the screw connector formed at least by the first lumen, and
the first connecting element and the second connecting element each being configured to form a gas-tight and/or a liquid-tight seal between the external environment of the screw connector and the interior of the screw connector when the inside thread is screwed to the outside thread in a third angle-of-rotation range.

2. The screw connector according to claim 1, wherein the first formation is a local elevation on a thread flank of the outside thread.

3. The screw connector according to claim 1, wherein the recess in the base of the thread of the nut includes at least one through-opening between an interior of the nut and an exterior surrounding of the nut.

4. The screw connector according to claim 3, wherein the at least one through-opening includes a radial groove in an axial end face of the nut, and wherein the radial groove is open in a direction of the axial end face of the nut.

5. The screw connector according to claim 3, wherein the nut has at least one reinforcing rib arranged in an axial direction of the nut on an outer circumference thereof, and the at least one through-opening extends at least partially along the reinforcing rib.

6. The screw connector according to claim 1, wherein the first connecting element and the second connecting element are each configured as complementary halves of a Luer-Lock connector.

7. The screw connector according to claim 1, wherein the second connecting element has a sealing cap with a sealing structure.

8. The screw connector according to claim 7, wherein the first lumen is configured as a female half of the Luer-Lock connector and the sealing structure is configured as a male half of the Luer-Lock connector.

9. The screw connector according to claim 1, wherein the second connecting element has a second lumen and the nut is configured as a union nut.

10. The screw connector according to claim 9, wherein the first lumen is configured as a female half of the Luer-Lock connector and the second lumen is configured as the male half of the Luer-Lock connector.

11. A medical hose system having a screw connector according to claim 1, wherein the medical hose system includes a blood hose set for an extracorporeal blood treatment, with the blood hose set having a patient arterial hose and a patient venous hose, and with a patient end of the patient arterial hose and the patient end of the patient venous hose each being configured as a second connecting element.

12. The medical hose system according to claim 11, wherein the medical hose system includes a three-way connector with three connected lumens, with at least two of the three connected lumens each being configured as the first connecting element.

13. The medical hose system according to claim 12, wherein the medical hose system is configured for short-circuiting the patient end of the patient arterial hose and the patient end of the patient venous hose with the three-way connector.

14. The medical hose system according to claim 11, wherein the end of the patient arterial hose opposite the patient end of the patient arterial hose, and the end of the patient venous hose opposite the patient end of the patient venous hose, are each connected to a blood cassette for the extracorporeal blood treatment.

15. The medical hose system according to claim 11, wherein the medical hose system has at least one addition site for an addition of medical fluids, with the addition site being configured as the first connecting element for connection to a sealing cap configured as the second connecting element.

16. The screw connector according to claim 1, wherein the gas permeability facilitates a gas sterilization and/or a steam sterilization of a medical hose system associated with an extracorporeal blood treatment, with the medical hose system including a blood hose set having a patient arterial hose and a patient venous hose, and with the patient end of the patient arterial hose and the patient end of the patient venous hose each deign being configured as the second connecting element.

17. The screw connector according to claim 2,
wherein the local elevation is a nose or a lobe on an outside diameter of the outside thread.

* * * * *